(12) United States Patent
Kerschbaumer et al.

(10) Patent No.: US 6,964,567 B2
(45) Date of Patent: Nov. 15, 2005

(54) DENTAL CAMERA WITH MOUTHPIECE

(75) Inventors: Harald Kerschbaumer, Klaus (AT); Walter Pokorny, Thüringen (AT); Gottfried Rohner, Alstätten (CH); Graham Pye, Genk (BE)

(73) Assignees: Ivoclar Vivadent AG, Schaan (LI); Shade Analyzing Technologies, Inc., Darien, CT (US)

( * ) Notice: Subject to any disclaimer, the term of this patent is extended or adjusted under 35 U.S.C. 154(b) by 104 days.

(21) Appl. No.: 10/328,779

(22) Filed: Dec. 24, 2002

(65) Prior Publication Data

US 2003/0148243 A1    Aug. 7, 2003

Related U.S. Application Data

(63) Continuation of application No. 10/134,052, filed on Apr. 26, 2002, now abandoned.

(60) Provisional application No. 60/327,908, filed on Oct. 9, 2001, provisional application No. 60/312,306, filed on Aug. 14, 2001.

(30) Foreign Application Priority Data

Apr. 27, 2001 (DE) ............................... 101 20 717

(51) Int. Cl.[7] ............................................ A61C 19/10
(52) U.S. Cl. ...................................... 433/26; 433/140
(58) Field of Search ............................. 433/26, 29, 31, 433/140; 604/77; 128/201.26

(56) References Cited

U.S. PATENT DOCUMENTS

| | | |
|---|---|---|
| 3,436,157 A | 4/1969 | Adler et al. ................. 356/192 |
| 3,861,044 A | 1/1975 | Swinson, Jr. |
| 3,971,954 A | 7/1976 | Kleinberg et al. .......... 250/475 |
| 4,096,217 A | 6/1978 | Roll |
| 4,247,202 A | 1/1981 | Failes |
| 4,414,635 A | 11/1983 | Gast et al. |
| 4,575,805 A | 3/1986 | Moermann et al. |
| 4,623,973 A | 11/1986 | Hoffrichter et al. |
| 4,654,794 A | 3/1987 | O'Brien |
| 4,836,674 A | 6/1989 | Lequime et al. |
| 4,881,811 A | 11/1989 | O'Brien |
| 5,048,519 A * | 9/1991 | Kasama et al. ........ 128/207.14 |
| 5,055,040 A | 10/1991 | Clar |
| 5,124,797 A | 6/1992 | Williams et al. |
| 5,177,694 A | 1/1993 | Graham et al. ............. 364/526 |

(Continued)

FOREIGN PATENT DOCUMENTS

DE            33 45 465 A1      6/1985

(Continued)

Primary Examiner—Ralph A. Lewis
(74) Attorney, Agent, or Firm—Winston & Strawn LLP

(57) ABSTRACT

A dental camera and a mouthpiece attachment thereon. The camera has a light source and a light receiving element configured for receiving reflected light and producing an image based on the received light. The mouthpiece is mountable to the housing of the camera and is configured for contacting a patient's mouth for positioning the camera with respect to at least a portion of the mouth. The mouthpiece has a light channel associated with the light source for permitting the emitted light to reflect off a tooth in a patient's mouth and permitting the reflected light to travel into the receiving element. A wing extends radially from the light channel and is configured and dimensioned for placement between a lip and teeth of a patient for substantially blocking light from entering the light channel from outside the wing. A display on the housing is associated with the receiving element for displaying the image. A sound receiving element on the housing allows a dentist to record voice comments and store these in connection with the images.

29 Claims, 6 Drawing Sheets

U.S. PATENT DOCUMENTS

| | | | |
|---|---|---|---|
| 5,273,429 A | 12/1993 | Rekow et al. | |
| 5,305,741 A | * 4/1994 | Moles | 128/207.14 |
| 5,340,309 A | 8/1994 | Robertson | |
| 5,373,364 A | 12/1994 | Krzyminski | |
| 5,383,020 A | 1/1995 | Viellefosse | |
| 5,498,157 A | 3/1996 | Hall | |
| 5,570,702 A | 11/1996 | Forman | |
| 5,598,843 A | 2/1997 | Caisey et al | |
| 5,690,486 A | 11/1997 | Zigelbaum | |
| 5,745,229 A | 4/1998 | Jung et al. | |
| 5,754,227 A | * 5/1998 | Fukuoka | 348/231.6 |
| 5,759,030 A | 6/1998 | Jung et al. | |
| 5,766,006 A | 6/1998 | Murljacic | |
| 5,851,113 A | 12/1998 | Jung et al. | |
| 5,851,115 A | 12/1998 | Carlsson et al. | |
| 5,871,351 A | 2/1999 | Jung et al. | |
| 5,880,826 A | 3/1999 | Jung et al. | |
| 5,883,708 A | 3/1999 | Jung et al. | |
| 5,926,262 A | 7/1999 | Jung et al. | |
| 5,938,446 A | 8/1999 | Andersson et al. | |
| 5,961,324 A | 10/1999 | Lehmann | |
| 5,966,205 A | 10/1999 | Jung et al. | |
| 5,967,775 A | 10/1999 | Shahid et al. | |
| 6,007,332 A | 12/1999 | O'Brien | |
| 6,038,016 A | 3/2000 | Jung et al. | |
| 6,038,024 A | 3/2000 | Berner | |
| 6,040,903 A | 3/2000 | Jung et al. | |
| 6,111,650 A | 8/2000 | Rawicz et al. | |
| 6,118,521 A | 9/2000 | Jung et al. | |
| 6,124,936 A | 9/2000 | Okamoto | |
| 6,132,210 A | 10/2000 | Lehmann | |
| 6,157,454 A | 12/2000 | Wagner et al. | |
| 6,188,471 B1 | 2/2001 | Jung et al. | |
| 6,190,170 B1 | 2/2001 | Morris et al. | |
| 6,206,691 B1 | 3/2001 | Lehmann et al. | |
| 6,210,159 B1 | 4/2001 | Lehmann et al. | |
| 6,222,620 B1 | 4/2001 | Jung et al. | |
| 6,233,047 B1 | 5/2001 | Jung et al. | |
| 6,239,868 B1 | 5/2001 | Jung et al. | |
| 6,244,863 B1 | 6/2001 | Rawica et al. | |
| 6,246,479 B1 | 6/2001 | Jung et al. | |
| 6,254,385 B1 | 7/2001 | Jung et al. | |
| 6,264,470 B1 | 7/2001 | Jung et al. | |
| 6,276,933 B1 | * 8/2001 | Melnyk et al. | 433/26 |
| 6,750,971 B2 | 6/2004 | Overbeck et al. | 356/405 |

FOREIGN PATENT DOCUMENTS

| | | |
|---|---|---|
| DE | 37 06 473 CA | 10/1988 |
| EP | EU 0360657 | 9/1989 |
| EP | 1 252 859 A2 * | 10/2002 |
| WO | WO 86/03292 | 6/1986 |
| WO | WO 94/20011 | 9/1994 |
| WO | WO 99/56658 | 11/1999 |
| WO | WO 01/41632 | 6/2001 |

* cited by examiner

DENTAL CAMERA WITH MOUTHPIECE

CROSS-REFERENCE TO RELATED APPLICATIONS

This application is a continuation of U.S. application Ser. No. 10/134,052 filed Apr. 26, 2002, now abandoned, which claims the benefit of U.S. Provisional Application Nos. 60/327,908, filed Oct. 9, 2001, and 60/312,306, filed on Aug. 14, 2001, the content of which applications is hereby expressly incorporated herein by reference thereto.

FIELD OF THE INVENTION

The present invention relates to a dental camera and a mouthpiece therefor. More specifically, the invention relates to a dental camera and a mouthpiece configured for blocking light from entering the camera from outside of a patient's mouth.

BACKGROUND OF THE INVENTION

A conventional dental camera for determining the color of teeth is known from EP-A1-376 647. In a conventional device of this type, a light source irradiates an object such as, for example, a tooth. The reflected light is captured or sensed by an optic capture device and is conducted to a reflected light receipt element. The reflected light receipt element is, in this conventional arrangement, configured as a spectrometer. With this arrangement, it is possible to specify or evaluate the color of an object.

This conventional arrangement relies upon a capture or sensing of light which is reflected at an angle from the surface of an object. This conventional arrangement is, for all practical purposes, operable only to sense scattered light so that the actual effective rate of light capture or sensing is substantially low.

A diagnostic device for use in the dental field, disclosed in DE-OS 33 45 465, permits a co-axial capture or sensing of the light reflected from a tooth. In this conventional arrangement, a light guide rod is provided which is overlaid by two light guide elements. The reflected light is guided to a photo resistor, which registers the brightness of the reflected light. By means of a filter, the capture or sensing of the reflected light can be adjusted to the respective spectrum which is desired to be observed. In this conventional arrangement, a determination or evaluation of the grade of reflection from the teeth is possible; however, it is, for substantially all practical purposes, not possible to effect a color comparison of a tooth in order to thereby specify a suitable replacement tooth.

In connection with evaluation of color, it is especially important that the lighting situation be reliably reproducible. The light source comprises a predetermined emission spectrum and the reflected light receipt element that is, for example, a CCD-cell-operates at a predetermined spectral sensitivity. In connection with avoiding a false color sensing, it has become known to undertake a so-called white color comparison. A unit comprising a light source and a reflected light receipt element can be calibrated by use of such a white color comparison. The calibration is, of course, relevant for the respective unit only under the same lighting circumstances. If, for example, a bulb is used as a light source and a bulb exchange of the existing bulb for another bulb is necessary, a renewed or refreshed white color comparison must be undertaken. Also, in connection with such white color comparisons, the conventional diagnosis devices reveal only partial color deviations.

U.S. Pat. No. 6,246,471 teaches a unit for measuring color. The unit has a display that displays data on color and optical properties or status or other information.

There is a need for a dental camera that facilitates the process of producing images of a portion of a patient's mouth, particularly for analyzing the color of teeth.

SUMMARY OF THE INVENTION

The present invention offers a solution to the challenge of providing a dental camera which makes possible a reliable and precise color evaluation and, especially, is operable independent of the hand-held position of the dental camera.

In a preferred embodiment, a mouthpiece attachment for a dental camera includes a body having a light channel associated with the camera for permitting passage of light therethrough to the camera. A first attachment portion of the mouthpiece body is configured for attaching to a second attachment portion of the dental camera with the light channel positioned to permit the passage of light to a light-receiving portion of the camera. The camera is configured, dimensioned, and has a weight for enabling hand-held operation with a single hand for producing images of the patient's teeth.

A wing preferably extends radially from the light channel and is configured and dimensioned for placement between a lip and teeth of a patient for substantially blocking light from entering the light channel from outside the wing when the mouthpiece is attached to the camera. The preferred wing extends radially from the light channel in a direction along the separation between the teeth of the upper and lower jaws of the patient and also radially from the light channel in a direction transverse to the separation between the teeth of the upper and lower jaws of the patient, most preferably extending radially substantially all around the light channel. This wing also has a distal surface that is substantially concave for placement against the teeth.

The attachment portion of one embodiment is substantially stiffer than the wing. A reference sample element is preferably provided in the mouthpiece and is configured for directing, and preferably reflecting, light with predetermined qualities to the receiving element for calibrating the camera and comparison to the color being analyzed in the patient's mouth. A blocking member of the mouthpiece is associated with the camera for substantially blocking entry of light between the camera and light channel from outside the camera, light channel, and patient's mouth, and the first attachment portion preferably comprises the blocking member.

A bite projection portion of the mouthpiece body extends adjacent to and from the wing of the preferred embodiment and is configured and dimensioned for biting by the patient to stabilize and position the camera. Preferably this bite projection portion extends on each lateral side of the light channel. The bite projection portion can be configured and dimensioned for positioning the light channel and teeth with respect to each other for producing images of the teeth based on the light passed through the light channel to the receiving portion.

A light receiving element of the preferred camera is configured for receiving light and producing an image base on the received light. A second attachment portion of the camera is configured for attaching to the first attachment portion for positioning the mouthpiece with respect to the receiving element for permitting the passage of light through the light channel to the receiving element. The preferred dental camera also has a light source, preferably a white light, configured and disposed for emitting light through the light channel for reflecting off a tooth of the patient and back through the light channel to the receiving element.

In the preferred embodiment, the light channel defines an opening extending through the channel. The width of the light channel is sufficient for allowing passage of sufficient light therethrough to the receiving element reflected from at least two teeth of the patient to form an image of the at least two teeth.

The preferred camera includes an image transfer member for transferring the image to a color analyzer for determining the color of the portion of the patient's mouth. Also, the camera may have color analyzing electronics mounted to the camera housing and connected to the receiving element for receiving the image and configured for determining the color of the portion of the patient's mouth. A processor and associated input keys for operating the camera are also mounted to the preferred housing.

The preferred embodiment also includes a display mounted to the housing and associated with the receiving element for displaying the image. The display can be movably mounted to the housing for tilting to adjust an angle between the light channel and the display. The display is preferably mounted to the housing in a position in which the image on the display is viewable from a side of the housing opposite from the light channel.

In another embodiment of the dental camera, the housing has a first elongated portion and an elongated handle connected to the elongated portion at an angle thereto, with the mouthpiece mounted at an end of the first elongated portion. The display of this embodiment is preferably mounted at an end of the elongated portion opposite from the mouthpiece.

The dental camera also preferably has a sound receiving element configured for receiving sound for storing in association with the image. A storage medium is preferably mounted to the housing and connected with the light and sound receiving elements for recording image and sounds in association with each other.

BRIEF DESCRIPTION OF THE DRAWINGS

Further details, advantages, and features of the dental camera of the present invention are provided in the hereinafter following description of one embodiment of the dental camera taken in connection with the figures of the drawings, in which.

DETAILED DESCRIPTION OF THE PREFERRED EMBODIMENT

Figure 1:
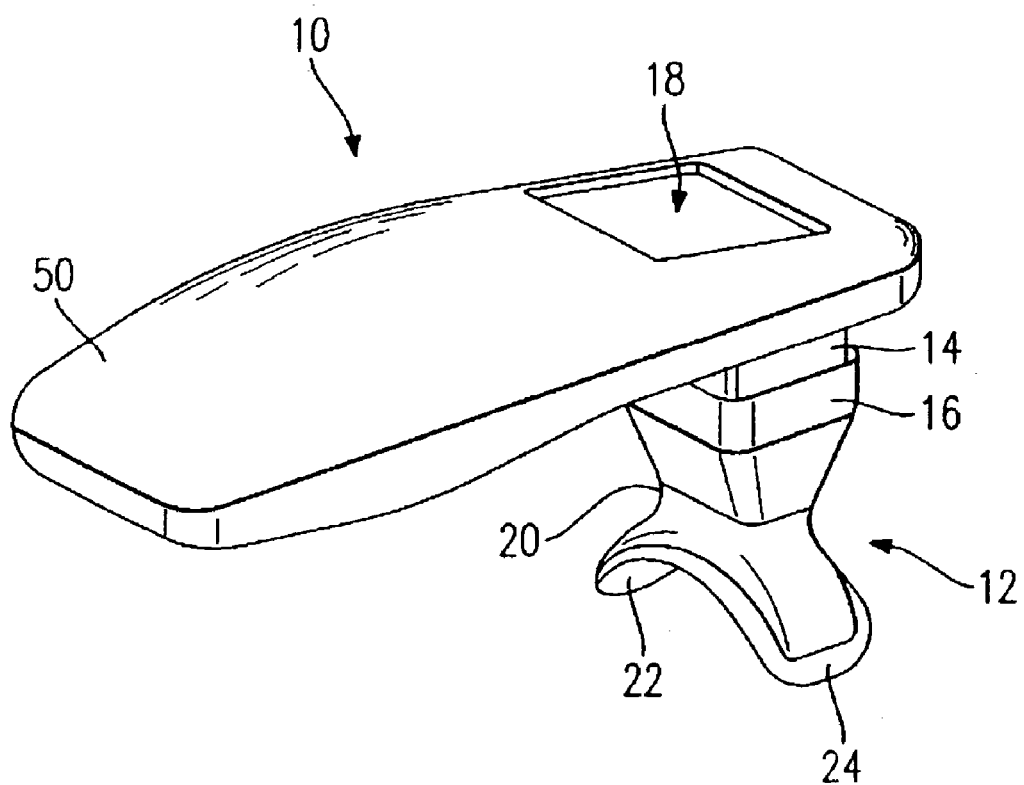
FIG. 1 is a perspective view of an embodiment of a dental camera constructed according to the present invention.

The dental camera of the present invention permits, in a surprising manner, the possibility to reliably determine, with simple means, the color trueness of an object. In accordance with the present invention, a mouthpiece is provided which, in the conventional manner of a mouthpiece, permits the disposal thereof in the space between the lips of a patient and, in this manner, ensures the blocking off of undesired light which is different than the light specified for the operation. In contrast, undesired outside light typically enters into and irradiates a mouth region of a patient if an annular pipe or conduit passes through the space between the patient's lips for the reason that a complete sealing around the space between the lips is not possible. In accordance with the present invention, it is provided that the light solely falls upon the reflected light receipt element; however, it is also preferably provided that only light from the light source passed through the mouthpiece falls upon the tooth so that a false reading corrupted by undesired outside light will not occur.

In a particularly advantageous embodiment of the dental camera of the present invention, the mouthpiece operates also to provide reference points for the orientation of the dental camera relative to the tooth of interest. These reference points function at the same time as spacer or standoff distance fixing elements so that the dental camera is always centered and fixedly positioned at the same uniform standoff distance from the tooth surface. The analysis of front teeth by the camera at a fixed and centered uniformed standoff distance is possible without additional measures by the provision of bite projections which extend from side wings of the mouthpiece to the teeth and are each horizontally oriented. Preferably, the dental camera includes a flat display screen for permitting the exact positioning of the camera in the horizontal direction which thus permits the immediate recognition or identification of the tooth which is to be evaluated.

Preferably, a CCD sensor or other suitable sensor is provided for receipt of the picture, whereby the selected reflected light receipt element is characterized by a good resolution of the captured picture. The dental camera also operates, in this connection, to intermediately store the received picture or, in accordance with another configuration of the inventive dental camera, to immediately transfer the received picture via an interface, which is connected in either a wireless manner or a wired manner, to a further location for evaluation of and follow up work on the picture.

Preferably, the mouthpiece includes a flat right-angled opening which is dimensioned such that it permits the simultaneous evaluation of at least two teeth. The light source is preferably integrated into the dental camera and its emission of light follows in a substantially co-axial manner with the receipt of reflective light through the opening in the mouthpiece so that the creation of shadows is prevented. A conventional polarization filter can be provided to shut out or preclude undesirable reflections.

Also, while it is possible to provide for the transfer or through passage of light through the mouthpiece via a light guide element, it is preferable to provide solely one open channel through which the light passes. Preferably, the reflected light receipt element is then blocked off by conventional black side walls so that no immediate or direct irradiation of the reflected light receipt element by the light from the light source can occur. It is also possible to couple the light source to a light guide element and to undertake the light irradiation of the object to be evaluated—that is, for example, the tooth—in a direct manner relative to this object so that special measures for blocking off the reflected light receipt element against false light are not necessary.

The outer configuration of the mouthpiece in the region of the lip gap is preferably also of a flat right-angled geometry with rounded-off corners. Also, if this outer configuration does not fully permit a complete sealing off from the lips, the penetration of false light still need not be feared as the opened area is covered by the side wings of the mouthpiece which each extend to respective sides of the mouthpiece opening.

The mouthpiece can be comprised of any suitable desired material such as, for example, plastic or polymeric material, whereby a black color or, at least, a non-light transmitting color, is preferred. The mouthpiece is, for hygienic reasons at least, preferably disposable and is mountable via a coupling to the dental camera. The inner radii of the mouthpiece are configured to be relatively large so that a cleaning of the mouthpiece is relatively easy.

As explained above, a color reference sample is preferably integrated into the mouthpiece by which a color evaluation of the tooth with the camera can be conducted such that a calibration of the camera is possible. The color evaluation follows after the camera is focused on the row of teeth following the positioning of the mouthpiece in the mouth of the patient, with the assistance of the bite projections or other distance standoff fixing elements. Preferably, the mouthpiece is comprised of at least two plastic materials having differing hardness or differing elastic properties in order to ensure an optimal disposal or mounting of the mouthpiece on the teeth structure and relative to the gums. As suitable material, rubber, silicone, or other plastic materials having a hardness up to that of elastic polymeric materials can be considered.

As seen in FIG. 1, a dental camera 10 of the present invention includes a mouthpiece 12 which extends forward at a transverse orientation from a front side of the dental camera. In this connection, a attachment coupling 14 is provided, which is encircled by a coupling sleeve 16 of the mouthpiece 12 in a light-sealing manner and is removable therefrom. The preferred camera is configured and dimensioned and is sufficiently light to permit handheld operation of the camera, preferably with a single hand, for taking pictures of teeth of a patient.

The dental camera 10, comprises an overall flat right-angled configuration with rounded-off corners. On the back of the dental camera, which is the upper side and turned toward the dentist or dental technician during operation, a display screen 18 is provided which displays the just received picture. The display screen 18 is preferably configured as a commercially available liquid crystal display, although other types of displays may be used. The preferred display 18 includes a color display screen, which in the embodiment shown is fixed to the camera housing 50.

Figure 3:
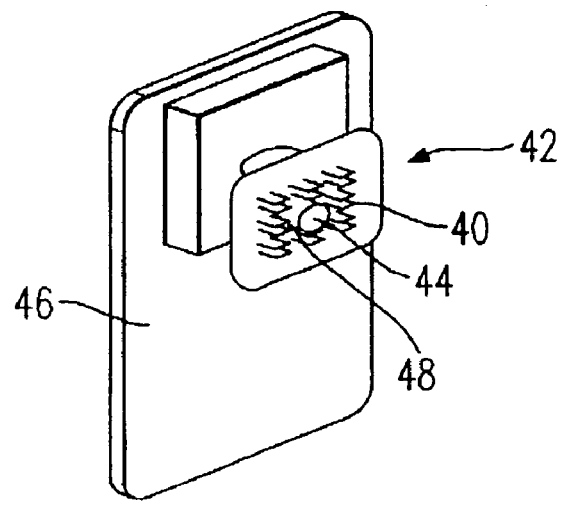
FIG. 3 is a unit of the camera with a light source and a reflected light receipt element.

The dental camera 10 includes a reflected light receipt element as well as a light source, as shown in FIG. 3. Furthermore, the dental camera 10 includes a connection for the transfer of the received pictures in data form to a computer which can be configured for the evaluation of, and the follow up work on, the pictures. Additionally, the dental camera includes a suitable voltage supply such as, for example, a battery or an accumulator, so that a cordless operation of the camera is also possible and the hand deployment of the camera is facilitated.

Figure 4:
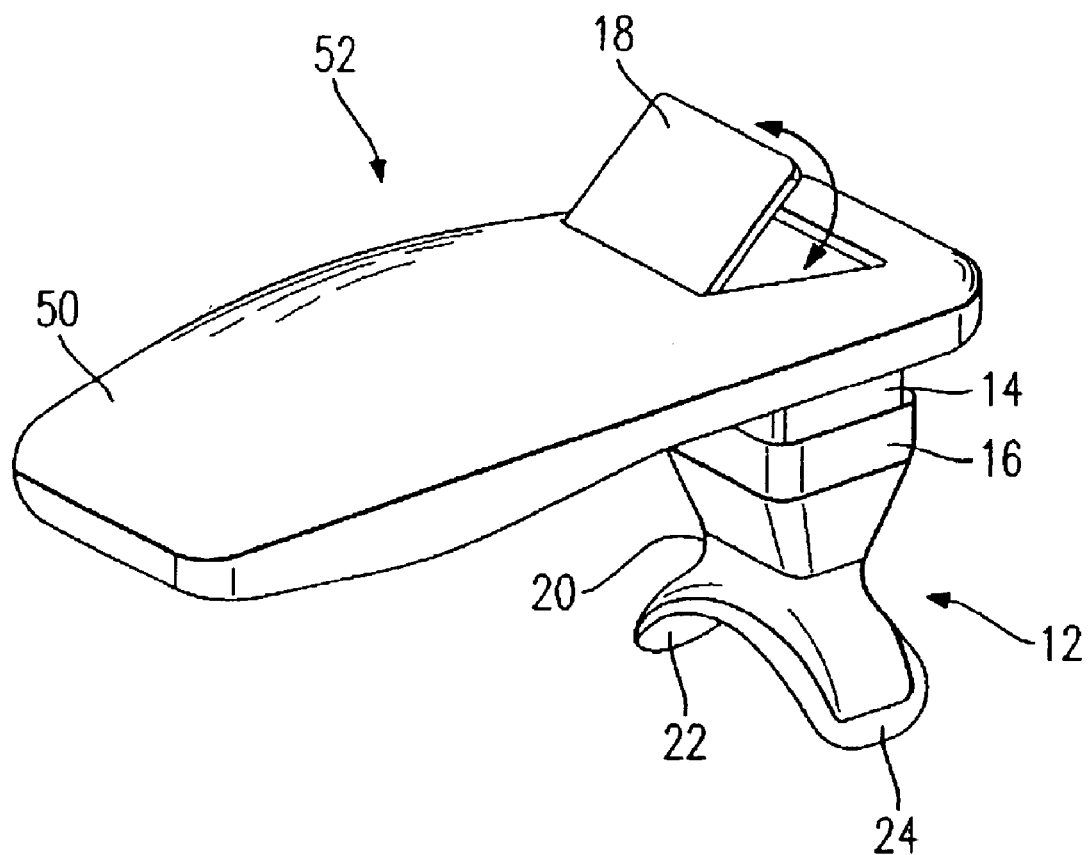
FIG. 4 is a perspective view of another embodiment of a dental camera with a tiltable display.

In the embodiment of the dental camera 52 shown in FIG. 4, the display screen 18 is pivotably mounted so that the display screen can be tilted to accommodate the viewing angle of the operator. In FIG. 4, the display is pivotable about an axis that is transverse to the longitudinal length of the housing 50, but in other embodiments, the display is pivotable with respect to the housing about one or more axes that may be different than the one shown in FIG. 4.

While the configuration of the embodiment of the dental camera 10 shown in FIG. 1 comprises a right-angled orientation of the coupling 14 relative to the camera, it is to be understood that other suitable configurations are possible. For example, it is possible to select the angled orientation of the coupling 14 relative to the balance of the dental camera 10 or to the housing 50 such that the coupling 14 extends at a non-right angle to the longitudinal extension of the main body of the dental camera 10. In a further modification of the one embodiment of the dental camera, it is provided that the position of the coupling 14 relative to the main body of the dental camera 10 can be adjusted.

The body of the dental camera 10 supports the mouthpiece 12 in a manner such that the mouthpiece 12 can be removed therefrom only by the application of a considerable force such as, for example, a force of 100 newtons. In this manner, it is ensured that the mouthpiece 12 cannot inadvertently be detached from the camera body while in the mouth of a patient. The attachment coupling 14 of the housing 50 and the coupling sleeve 16 of the mouthpiece 12 preferably have corresponding shapes and attach together with a press-fit, where at least one of the coupling 14 and coupling sleeve 16 is resiliently deformable and has a blocking member to block light from entering from outside the housing 50 or mouthpiece 12. Preferably, the coupling sleeve 16 is resiliently stretched about the coupling 14 when the mouthpiece 12 is attached to the housing 15.

The coupling 14 has a substantially large inner diameter or cross-section. In contrast thereto, the mouthpiece 12 tapers down in the area of the lips to form a lip through passage channel 20. In this area, the outer diameter or cross-sectional dimension is preferably substantially flat and right-angled, with curved edges, and is approximately 1 centimeter in height. The mouthpiece 12 preferably includes two side wings 22 and 24 extending transversely and radially from the channel 20 in a curved manner, following the tooth curvature of the patient.

Referring to FIG. 1, the mouthpiece 12 is configured and has a stiffness for positioning the object location, where the teeth to be imaged are located during imaging, at a proper focal length for the dental camera. The camera preferably has adjustable focusing lenses that can focus on the teeth within a range of object locations. The side wings 22,24 are, however, substantially more flexible and softer than the middle region of the mouthpiece and the channel portion 20. The side wings 22,24 extend in a rounded-off manner with rounded edges so that the danger of injury to a patient is exceptionally low. The mouthpiece 12 is preferably formed of a soft rubber or other suitable materials.

Figure 2:
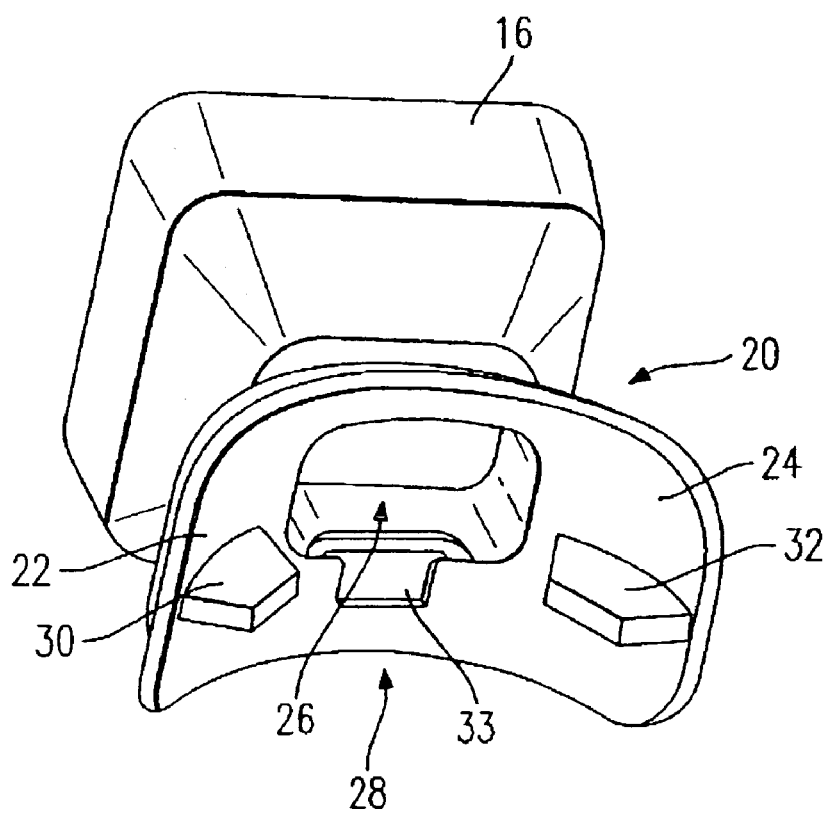
FIG. 2 is a perspective view of a mouthpiece thereof.

Referring to FIG. 2, the mouthpiece 12 includes an opening 26 which extends into the middle region 28 of the mouthpiece 12. The opening 26 is, in correspondence with the configuration of the lip through passage channel 20, configured in a fat right-angled configuration with rounded-off corners. The channel 20 is configured and dimensioned for a human patient's lips to fit comfortably around the channel 20 with the patient's mouth substantially closed.

As can be seen in FIG. 2, each of the side wings 22,24, on each lateral side of the channel 20, is provided with a bite projection 30,32, respectively. In this manner, a firm fixing of the position of the mouthpiece 12 and consequently of the dental camera 10 can be effected without further measures. The bite projections 30,32 also act as spacers and have a thickness and stiffness selected to space the teeth as desired. The bite projections 30,32 preferably extend from and adjacent the wings 22,24 and are configured and dimensioned so the patient can bite on them to stabilize and position the camera in a proper position for taking a picture of the desired teeth. In the preferred embodiment, the bite projections 30,32 are disposed at a height, with respect to the patient's mouth while bitten by the patient during use, substantially centered with respect to the channel 20. In an alternative embodiment, the bite projections are disposed off center, preferably both towards the top of the channel with respect to the center of the channel, or both towards the bottom of the channel. Other arrangements and numbers of bite projections can also be provided to change the desired position of the camera and channel with respect to the teeth, for example to take pictures of only the upper or lower teeth or of other parts of the mouth.

In the embodiment of FIGS. 1–3, the upper as well as the lower front teeth can be irradiated and the light reflected thereby can be received by the dental camera 10 in that the bite projections 30,32 are each arranged approximately in the vertical middle and the receipt field as explained above. The thickness and stiffness of the bite projections 30,32 is selected to properly position the camera. In this embodiment, at least two teeth, and more preferably at least four teeth, can be simultaneously irradiated, imaged, and evaluated, and it is possible to obtain a picture image of the irradiated teeth, which is accommodated to the desired color specification requirements. More than half of each of the imaged teeth is preferably imaged, and more preferably each of these teeth is imaged in their entirety.

The middle region 28 of the mouthpiece 12 includes a receipt slot for mounting a reference sample element 33 to the dental camera which is immediately neighboring the tooth to be evaluated. In this manner, a direct color comparison is possible between the teeth and the sample element 33. The sample element 33 can also be used for calibrating the receiving element as the sample element can be of a predetermined color. The preferred sample element is white, and is a different color than the part of the mouthpiece 12 and remainder of the camera 10 that is visible by the receiving element. The sample element 13 is also preferably mounted generally transversely to the axis of the light channel 20.

In the illustrated this embodiment of the dental camera of the present invention, the opening 26 is configured as a through passage. It is to be understood that, without the provision of any further means, it is possible to provide a protection screen in order to protect the reflected light receipt element shown in FIG. 3, such as from items from the patient's mouth. Also, in any desired suitable manner, the receipt optics can be provided, for example, through the opening 26 or by additional lenses or the like. It is also possible to connect light guide element or a light guide rod to the reflected light receipt element.

As shown in FIG. 3, an arrangement for receipt and production of the light is preferably comprised of eight light diodes or laser diodes 40, which collectively form a light source 42 that is arranged preferably in an annular manner around a reflected light receipt element 44. The light source 42 and the reflected light receipt element 44 are mounted on a base unit 46 in a fixed relative position to each other. By means of the annular arrangement of the light diodes 40, a shadow-free illumination of the area to be evaluated is possible.

It is to be understood that the light source can be configured in any desired suitable manner. For example, diodes producing lights of three colors can be used, such as green, blue, and red light diodes distributed in a uniform manner around the receiving elements of the light receipt element 44 in order to emit a white light.

The light receipt element 44 preferably includes a CCD element for acquiring an image based on the reflected light that it receives. Electronics in the housing 50 control the light source 42, as well as the CCD and operation of the display 18 and of an image storage medium, which is preferably contained within the housing.

It is also possible to use white light diodes or other different suitable light sources. A small tube or conduit 48 extends around the reflected light receipt element 44 and extends in a forward manner to the coupling 14, past the diodes 40 of the light source, and the coupling member and walls surrounding the light source and light receipt elements are preferably configured for substantially preventing light from reaching the receipt element that has not been reflected off the user's mouth. In this manner, a false lighting of the reflected light receipt element by the non-reflected light directly from the light source 42 is substantially eliminated.

Figure 5:
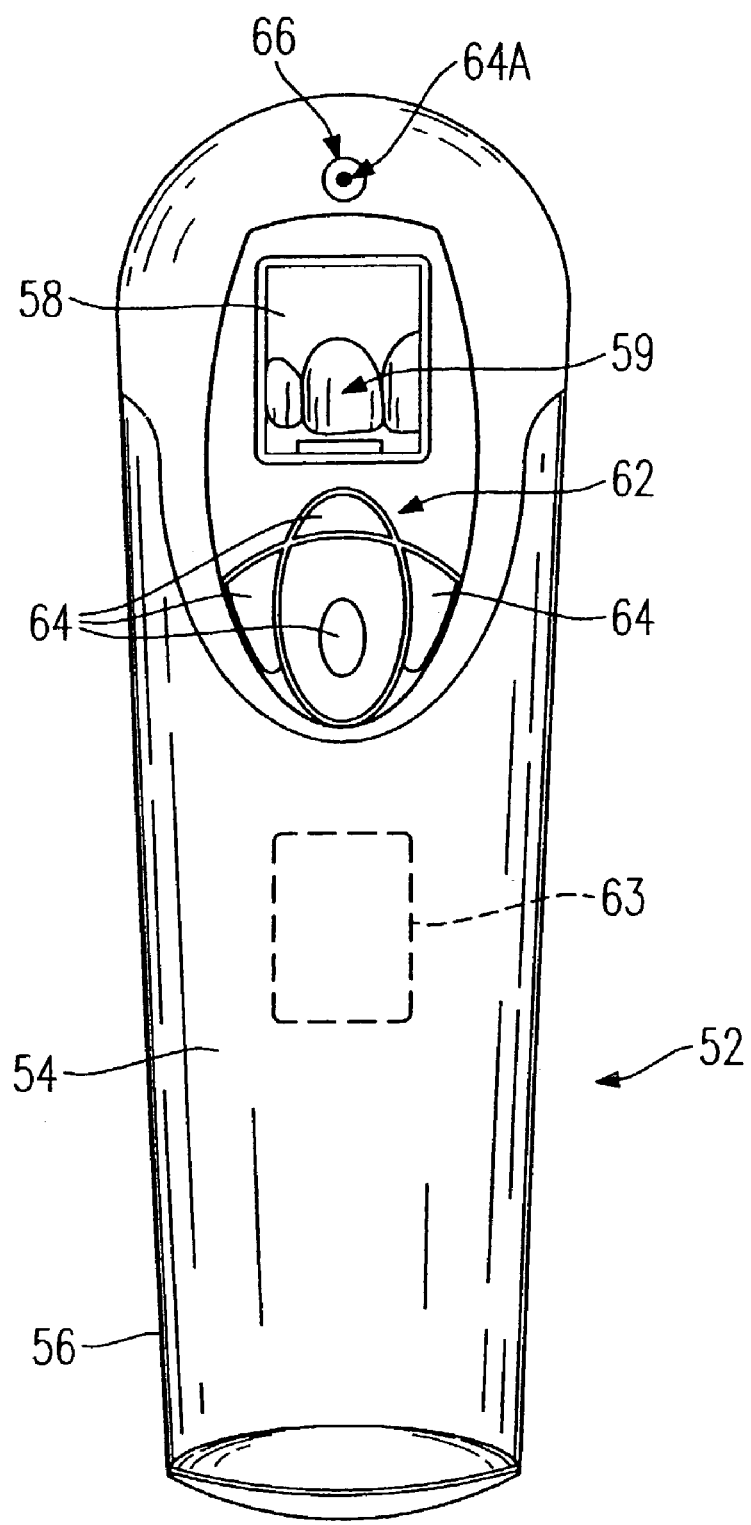
FIGS. 5 and 6 are rear and rear perspective views of another embodiment of a dental camera with input keys.
Figure 6:
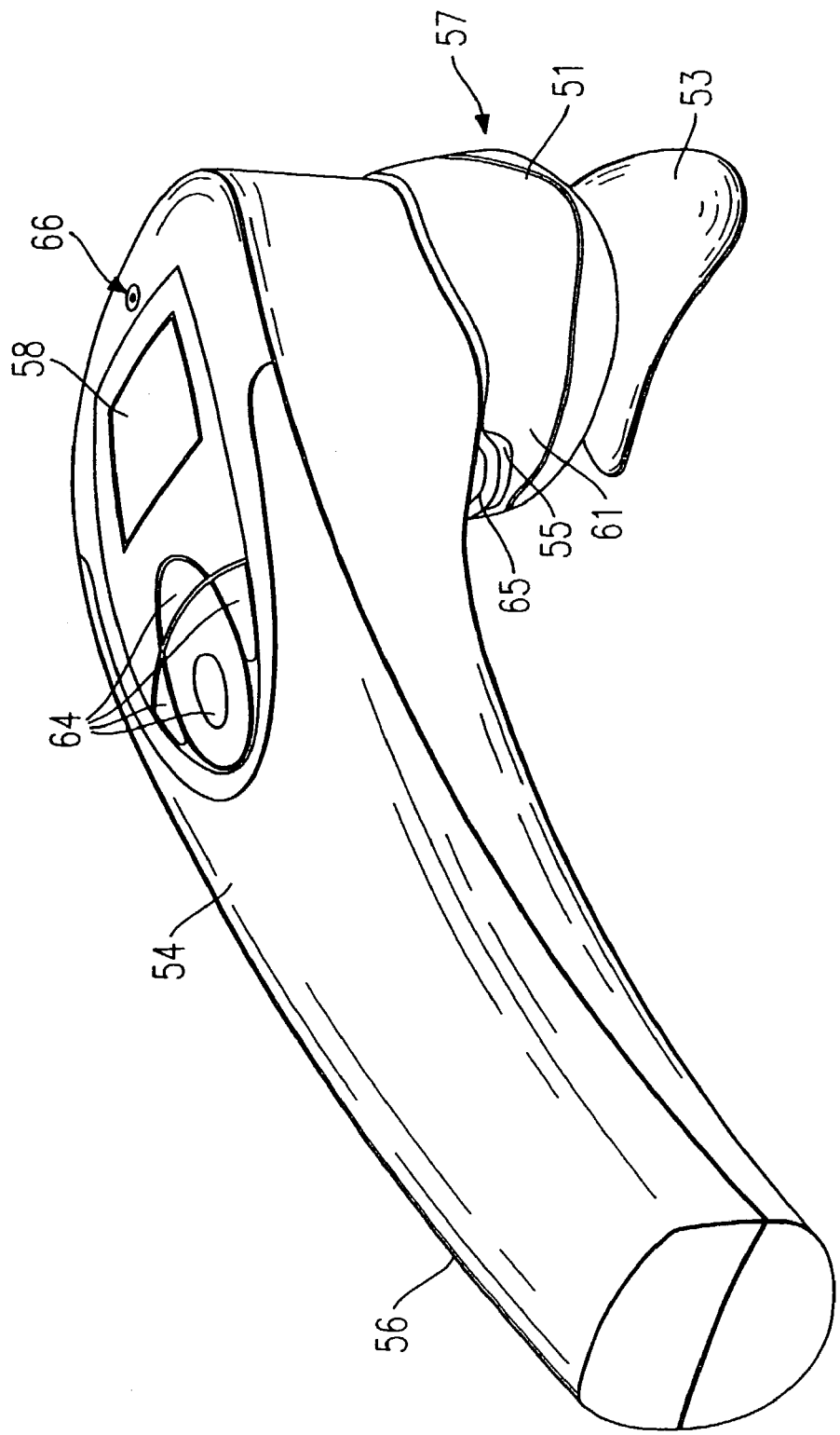

Referring to FIGS. 5 and 6, another embodiment of a dental camera 52 with a housing 54 that has a handle portion 56 extending below a mouth interface portion 57. Mouthpiece 60 has a coupling sleeve 61 with a rounded, preferably cylindrical or conical shape, attached to a correspondingly shaped attachment coupling of the housing 54. The attachment coupling and mouthpiece 51 have axes oriented at an angle with respect to the handle portion 56 of preferably more than about 30°, more preferably more than about 45°, more preferably more than about 70° or at or substantially at about a right angle to the axis thereof. The handle portion 56 is preferably tapered and shaped for easy gripping and single handed handling, preferably such that the palm of the hand can fit around the lower portion of the handle, with the thumb resting on keys 64, which are described below. The mouthpiece has radially extending wings 53. The housing 54 and coupling sleeve 61 define a finger engageable portion 55, which preferably comprises a protruding tab 65 that protrudes from the coupling sleeve 61 sufficiently to facilitate engagement with a finger tip to release the mouthpiece 51 from the housing 54.

Color display 58 is disposed on the back of the housing 54 and is visible by an operator when the front side is received in a patient's mouth. The display is configured to show the image 59 acquired by the light reception element and specific photographs that are taken, as well as operational data and user operable menus and information about the image.

Preferably adjacent and most preferably below the display is a control portion 62, which includes a plurality of keys 64 or other user interface. The keys 64 are positioned for operation by the same hand of the user that holds the camera 52. As shown in FIG. 6, the keys of this embodiment are positioned within reach of the thumb, with the remaining fingers and palm of the user grasping the handle portion 56. The keys 64 control the operation of the camera, including the image acquisition and the display thereof, voice recording as described below, camera power, shutter or CCD operation, operational menu control, mode selection, and operational help information.

A sound receiving element, such as a microphone 64, is disposed in a position for capturing the voice of the camera operator. Associated electronics and storage are provided inside the housing for recording the voice messages. The electronics are preferably configured for associating or linking the voice to particular images, so that oral notes can be stored in connection with each image, reducing the time it takes to annotate each image. The images and associated sound recordings can preferably be recalled together.

Also contained within the housing 54 are preferably a power storage element 63, such as a battery or accumulator, and electronics for displaying the image produced, for controlling the lights and optics and for storing captured images in a storage medium or memory, which is also preferably housed in the housing 54. The storage medium may be a digital storage medium and is preferably the same one used for storing the voice recordings. A speaker 66 is preferably also provided to play beck back recordings with the images. A connector 67 is disposed at the bottom of the handle 56 for transferring image, sound, operational, and other data as necessary to a computer, modem, or a network. The connector also preferably includes a provision to charge the camera power supply, or to plug into an external supply and can comprise a USB interface connected to a smart media card, which are known in the art.

Figure 8:
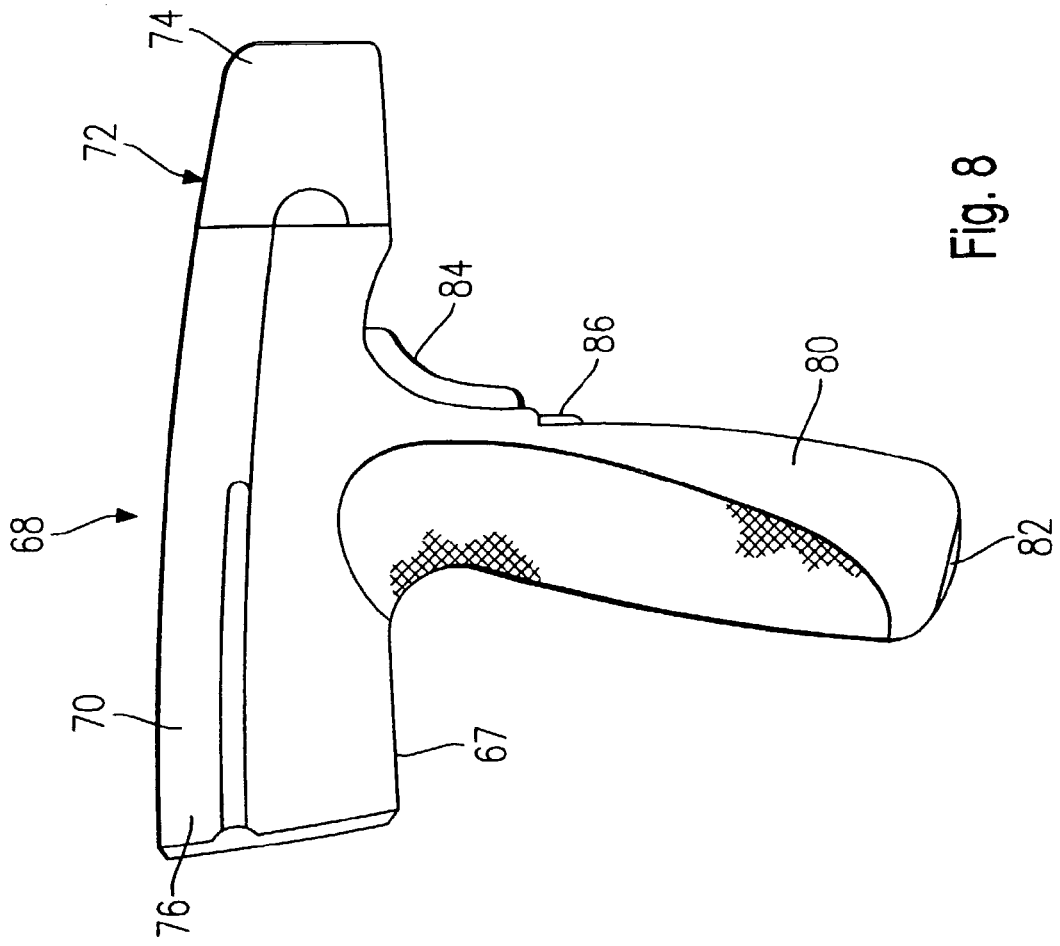
FIGS. 7 and 8 are rear and side views of another embodiment of a dental camera with a handle that extends at an angle to the main camera body.
Figure 7:
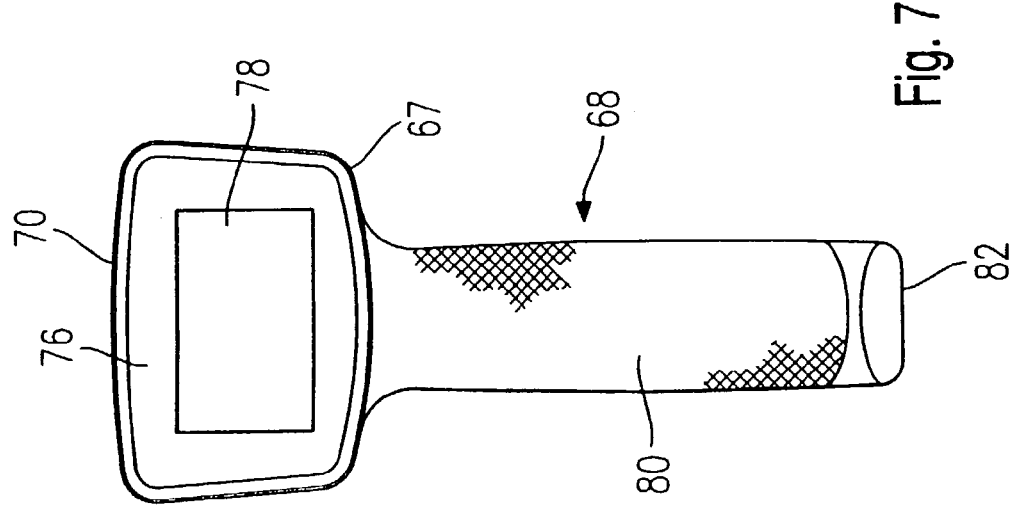

Referring to FIGS. 7 and 8, housing 67 of camera 68 has a main camera body 70 of an elongated shape. A front end 72 of the main body 70 connects to mouthpiece 74, which in the embodiment shown is a soft rubber member without wings. Alternatively, wings as described in the previous embodiments may be employed. The light source and receipt element are arranged to emit the light and receive the reflected light through the front end 72 to obtain an image of the patient's teeth. Preferably the light source and the receipt element are disposed in or near the front end 72, and light conduits, such as fiber optics may be employed to guide the light as necessary. At a back end 76 of the main body 70, opposite from the mouthpiece 74, is a rearward-facing display 78.

An elongated handle 80, generally having a pistol grip configuration, is connected to the main body 70 at an angle thereto, preferably substantially transversely. The handle preferably extends from a location near the center between the front and back ends 70,76 of the main body 70, but may alternatively be disposed adjacent or at one of the ends. A connector 82 is disposed at the bottom of the handle 80 for transferring image, sound, operational, and other data as necessary to a computer, modem, or a network.

A trigger 84, preferably depressible into the handle, is disposed near the intersection of the main body 70 and the handle 80, and may alternatively extend from the main body 70. The trigger is preferably employed to control the optical assembly to acquire and store the image that is presently displayed on the display 78. The trigger can also serve other functions, such as selection of operational menu items that are displayed on the display 78. The trigger 84 is preferably disposed and operable as a pistol trigger, easily falling within reach of an index finger of the user. Additional keys 86 are also preferably provided for controlling other operations of the camera.

While illustrative embodiments of the invention are disclosed herein, it will be appreciated that numerous modifications and other embodiments may be devised by those skilled in the art. Therefore, it will be understood that the appended claims are intended to cover all such modifications and embodiments that come within the spirit and scope of the present invention.

What is claimed is:

1. A dental camera mouthpiece, comprising a body that comprises:
    a light channel associable with a dental camera for permitting passage of light therethrough to the camera;
    a first attachment portion configured for attaching the body to the camera with the light channel positioned to permit the passage of light to a light receiving element of the camera;
    a wing extending radially from the light channel and configured and dimensioned for placement with respect to lips and teeth of a patient for substantially blocking light from entering the light channel from outside the wing when the mouthpiece is attached to the camera;
    a reference sample element configured for directing light with predetermined qualities to the light receiving element for calibrating the camera, and
    an attachment portion configured and dimensioned for removably mounting the reference sample element, wherein the color of the reference sample element is a white color.

2. A dental camera, comprising:
    a light receiving element, which is configured for receiving light and producing an image based on the received light;
    a mouthpiece, comprising a body that comprises:
        a light channel associable with the camera for permitting passage of light therethrough to the camera,
        a first attachment portion configured for attaching the body to the camera with the light channel positioned to permit the passage of light to the light receiving element of the camera, and
        a wing extending radially from the light channel and configured and dimensioned for placement with respect to lips and teeth of a patient for substantially blocking light from entering the light channel from outside the wing when the mouthpiece is attached to the camera; and
    a second attachment portion configured for attaching to the first attachment portion for positioning the mouthpiece with respect to the light receiving element for permitting the passage of light through the light channel to the light receiving element.

3. The dental camera of claim 2, wherein the first attachment portion is substantially stiffer than the wing.

4. The dental camera of claim 2, wherein the mouthpiece attachment portion comprises a blocking member associable with the camera for substantially blocking entry of light between the camera and light channel from outside the camera, light channel, and patient's mouth.

5. The dental camera of claim 2, wherein the mouthpiece further comprises a bite projection portion extending adjacent the wing and configured and dimensioned for biting by the patient to stabilize and position the camera with respect to the mouth.

6. The dental camera of claim 5, wherein the bite projection portion extends from the wing.

7. The dental camera of claim 6, wherein the bite projection portion extends on each lateral side of the light channel.

8. The dental camera of claim 2, wherein the light channel defines an opening extending through the channel.

9. The dental camera of claim 2, wherein the wing extends radially from the light channel in a direction along the separation between the teeth of the upper and lower jaws of the patient.

10. The dental camera of claim 9, wherein the wing extends radially from the light channel in a direction transverse to the separation between the teeth of the upper and lower jaws of the patient.

11. The dental camera of claim 2, further comprising a light source configured and disposed for emitting light through the light channel and upon one or more teeth of the patient, and for receiving light that is reflected from the one or more teeth and directing the received light back through the light channel to the receiving element.

12. The dental camera of claim 2, wherein the light channel has a width sufficient for allowing passage therethrough of sufficient light reflected from at least two teeth of the patient back to the receiving element to form an image of the at least two teeth.

13. The dental camera of claim 2, wherein the camera is configured, dimensioned, and has a weight for enabling handheld operation with a single hand for producing an image of the patient's tooth or teeth.

14. The dental camera of claim 2, wherein the first and second attachment portions are separably attachable to each other.

15. The dental camera of claim 2, wherein the wing has a distal surface that is substantially concave for placement against the teeth.

16. The dental camera of claim 2, wherein the mouthpiece body includes a reference sample element with predetermined reflective qualities and disposed for reflecting the emitted light to the receiving element adjacent the light reflected from the teeth.

17. The dental camera of claim 2, further comprising an image transfer member for transferring the image to a color analyzer for determining the color of a portion of the patient's mouth.

18. The dental camera of claim 2, further comprising:
a housing associated with the light receiving element and second attachment portion; and
color analyzing electronics mounted to the housing and connected to the receiving element for receiving the image and configured for determining the color of a portion of the patient's mouth.

19. The dental camera of claim 18, further comprising:
a processor mounted to the housing; and
input keys connected with the processor for operating the camera and color analyzing electronics.

20. The dental camera of claim 2, further comprising:
a housing; and
a display mounted to the housing and associated with the receiving element for displaying the image.

21. The dental camera of claim 20, wherein the display is movably mounted to the housing for tilting to adjust an angle between the light channel and the display.

22. The dental camera of claim 20, wherein the display is mounted to the housing in a position in which the image on the display is viewable from a side of the housing opposite from the light channel.

23. The dental camera of claim 20, wherein the housing comprises a first elongated portion and an elongated handle connected to the elongated portion at an angle thereto, wherein the mouthpiece is mounted at an end of the first elongated portion.

24. The dental camera of claim 23, wherein the display is mounted at an end of the elongated portion opposite from the mouthpiece.

25. The dental camera of claim 20, further comprising a sound receiving element configured for receiving sound for storing in association with the image.

26. The dental camera of claim 25, further comprising a storage medium mounted to the housing and connected with the light and sound receiving elements for recording images and sounds in association with each other.

27. A dental camera mouthpiece, comprising:
a light channel associable with a camera housing for permitting passage of light therethrough to a receiving element,
a first attachment portion configured for attaching to the camera housing with the light channel positioned to permit the passage of light to the receiving element,
a wing extending radially from the light channel and configured and dimensioned for placement with respect to lips and teeth of a patient for substantially blocking light from entering the light channel from outside the wing when the mouthpiece is attached to the camera, and
a bite projection portion that is disposed on the wing and vertically off-center with respect to the light channel, and configured and dimensioned for placement between upper and lower teeth of a patient for positioning the light channel and teeth with respect to each other for producing images of the teeth based on the light passed through the light channel to the receiving element.

28. A dental camera, comprising:
a housing;
a light source mounted to the housing and configured for emitting light;
a receiving element mounted to the housing and configured for receiving reflected light and producing an image based on the received light;
a mouthpiece mounted to the housing and configured for contacting a patient's mouth for positioning the camera with respect to at least a portion of the mouth;
a light channel associated with the light source for permitting the emitted light to reflect off a tooth in a patient's mouth and permitting the reflected light travel into the receiving element; and
a sound receiving element configured for receiving sound for storing in association with the image,
wherein the mouthpiece comprises a wing extending radially from the light channel and configured and dimensioned for placement between a lip and teeth of a patient for substantially blocking light from entering the light channel from outside the mouth.

29. The dental camera of claim 28, wherein the camera is configured and dimensioned and is sufficiently lightweight for handheld operation for producing images of the patient's tooth or teeth.

* * * * *